United States Patent [19]

Leonard et al.

[11] Patent Number: 4,846,793
[45] Date of Patent: Jul. 11, 1989

[54] INJECTOR FOR IMPLANTING MULTIPLE PELLET MEDICAMENTS

[75] Inventors: Robert J. Leonard, Lynnfield, Mass.; S. Mitchell Harman, Ellicot City, Md.

[73] Assignee: Endocon, Inc., Boston, Mass.

[21] Appl. No.: 27,565

[22] Filed: Mar. 18, 1987

[51] Int. Cl.⁴ ............................................. A61M 31/00
[52] U.S. Cl. ....................................... 604/62; 604/60; 128/330; 221/244; 221/279; 206/537
[58] Field of Search .................. 221/244, 279, 22; 604/59-64, 51; 128/330; 206/536, 537

[56] References Cited

U.S. PATENT DOCUMENTS

| | | | |
|---|---|---|---|
| 939,693 | 11/1909 | Holtzmann | 604/60 X |
| 2,269,963 | 1/1942 | Wappler | 604/61 |
| 2,513,014 | 6/1950 | Fields | 604/60 |
| 2,718,299 | 9/1955 | Atwater et al. | 221/279 X |
| 2,761,446 | 9/1956 | Reed | 604/59 |
| 2,885,116 | 5/1959 | Toegilgas | 221/279 X |
| 3,992,796 | 11/1976 | Dorgnon | 42/90 |
| 4,086,914 | 5/1978 | Moore | 600/7 |
| 4,154,239 | 5/1979 | Turley | 604/61 |
| 4,174,048 | 11/1979 | Volpe, Jr. | 221/267 |
| 4,223,674 | 9/1980 | Fluent et al. | 604/51 |
| 4,451,253 | 5/1984 | Harman | 604/60 |
| 4,451,254 | 5/1984 | Dinius et al. | 604/62 |
| 4,666,103 | 4/1989 | Harman | 604/62 |
| 4,753,636 | 6/1988 | Free | 604/49 |

Primary Examiner—Martin P. Schwadron
Assistant Examiner—Allen J. Flanigan
Attorney, Agent, or Firm—Wolf, Greenfield & Sacks

[57] ABSTRACT

A device for subcutaneous implantation of a plurality of solid, elongated medicinal pellets. The device includes a needle-like, hollow cannula within a barrel. The hub has a manually engageable knob thereon so that the hub and cannula may be easily moved with respect to the barrel with the thumb of one hand during the implantation process. An obturator extends from the rear of the barrel into the proximal end of the cannula. The obturator is composed of two or more sections which allow it to telescope during operation.

16 Claims, 3 Drawing Sheets

INJECTOR FOR IMPLANTING MULTIPLE PELLET MEDICAMENTS

FIELD OF THE INVENTION

This invention relates to medicinal implants, and more specifically to devices for administering and implanting solid form medicaments subcutaneously.

BACKGROUND OF THE INVENTION

One method of administering medicines is by subcutaneously implanting a medicinal pellet. In the past, this form of administration of drugs was not widely used. Recently, however, materials have been developed which allow a drug to be subcutaneously introduced or administered beneath the skin of a patient so that the drug is slowly released over a long period of time. Such implants allow a drug to be dispensed in a relatively uniform dose over many months or years. This method of administering drugs is becoming especially important and popular as a method of administering contraceptive implants.

While subcutaneous implantation may be done surgically using a scalpel to make the incision and a trocar and cannula to place the implant, such methods require a physician or other highly trained person. Recently, improved instruments for implanting subcutaneous medicaments have been developed. These instruments have several advantages over surgical implantation. The instruments typically require far less skill to operate, and thus may be used by a paramedic or nurse. The instruments generally require less time to perform an implantation procedure.

Additionally, these instruments are frequently less intimidating and therefore more psychologically acceptable to a patient than are surgical procedures. This last advantage can be of great importance in some applications. For example, implantation of long term contraceptive devices is extremely attractive in many underdeveloped countries having an over-population problem. Typically, the potential subjects for administration of long term contraceptive implants in these countries are located in areas remote from modern medical care. The patients who could most benefit from such contraceptive methods are frequently unfamiliar with modern medicine and its techniques and instruments.

In such patients, the "intimidation factor" of an implantation procedure may be a major factor in whether or not a potential patient decides to accept the procedure. For these reasons, it is important that a device for performing subcutaneous implantation should be able to perform the desired implantation with minimal psycholoqical and physical trauma to a patient.

The materials in which contraceptive steroids are imbedded in subcutaneous implantation are normally biologically inert polymers, some of which are biodegradable. The pellets made from such materials are typically long and cylindrical in cross section, and the size of these materials is on the order of the size of a pencil lead. The materials are generally flexible ranging from somewhat flexible to very flexible nature. See, for example, U.S. Pat. No. 4,451,253 which describes some exemplary contraceptive pellets and an apparatus for individually implanting such pellets subcutaneously.

The size and shape of an implant pellet are important in determining the rate of delivery of a particular drug from a subcutaneous implant. Practical considerations put constraints on the dimensions which a subcutaneous implant may have. In particular, the length of an implant is generally limited. A typical implant is on the order of 1 ½ to 2 inches long. Longer implants are much more difficult to accurately locate. They are also more susceptible to breakage, which may affect the drug delivery rate and, in general, they are simply more cumbersome and cosmetically apparent. Because of this, it is frequently necessary to implant a desired amount of a drug as a plurality of individual, shorter implant pellets rather than as a single longer pellet. Thus, an instrument which can quickly allow a physician or nurse to implant a plurality of pellets with minimal physical and psycholoqical trauma to a patient would be desirable. When implanting several implants, care must be taken to accurately place the implants in a manner such that one does not interfere with the dissolution of the others.

SUMMARY OF THE INVENTION

Briefly, the present invention provides an improved device for subcutaneous implantation of a plurality of solid, elongated medicinal pellets. The device includes a needle-like, hollow cannula within which are located a plurality of medicinal implants. The cannula is attached to a hub which slides forward and backward within a barrel. The hub has a manually engageable knob thereon so that the hub and cannula may be easily moved with respect to the barrel with the thumb of one hand during the implantation process. An obturator extends from the rear of the barrel into the proximal end of the cannula. The obturator is composed of two or more sections which allow it to telescope during operation.

To place an implant, the cannula is inserted through the skin with the implants located within the cannula. Once the cannula is placed so that the first implant is in the desired location, the cannula is moved backward by means of the thumb knob while the barrel is maintained in a fixed position so that the operator causes the implant to remain in place under the skin as the cannula is withdrawn from around the implants. The obturator maintains the implant in place under the skin while the cannula is withdrawn from around the first implant.

At this point, the second implant is at the end of the cannula. The obturator in the present invention is designed to telescope as the barrel is pulled backward, relative to the cannula and hub, after the first implantation. Thus, when the barrel is pulled back, the cannula and hub are returned to their original position at the forward end of the barrel, and the obturator increases in length and locks in place. The injector may then be manipulated to locate the second implant alongside the first implant in a fan-shaped pattern. The cannula and hub are then moved toward the rear end of the barrel as before while the obturator in its extended position maintains the implant in place under the skin as the cannula is withdrawn from around th implant.

In this manner, two implants may be positioned quickly and easily through a single puncture site without having to remove the injector from the incision.

BRIEF DESCRIPTION OF THE DRAWINGS

The operation and advantages of the invention will become more clear upon reading the following description of the preferred embodiment in conjunction with the accompanying drawings of which.

DETAILED DESCRIPTION OF THE PREFERRED EMBODIMENT

Figure 1:
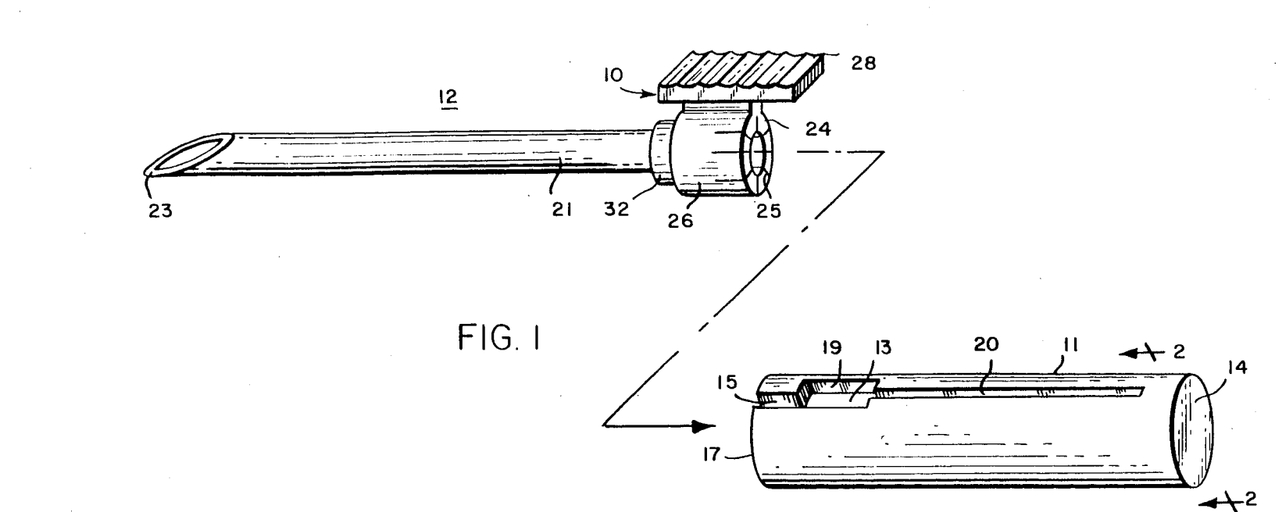
FIG. 1 is a perspective view showing barrel and needle assembly of the injector.

Referring to FIG. 1, there is shown in perspective a view of the present invention. The invention includes a barrel portion 11. Barrel 11 is open at the front end 17 thereof. The barrel 11 is cylindrical in shape and is typically formed of plastic by means of injection molding or other suitable process. The rear end 14 of barrel 11 is closed. A slot 20 extends from the front portion 17 of barrel 11 toward the rear and terminates just short of the rear wall 14 of the barrel.

A needle or cannula 21 is attached to a hub 26 to form a needle assembly 12. The outside diameter of Hub 26 fits inside the hollow portion of barrel 11, so that the hub slides forward and backward within the barrel. Cannula 21 is typically formed of surgical steel and has a bevel 23 at the distal end thereof. The bevel may be a "B" or "intravenous" cutting bevel of known type which allows the cannula to puncture the skin without a prior incision and without coring of flesh or body fluids. Other bevels may also be used. It should be clear that the described injector may also be used to implant medicaments through an existing incision made by other means.

Figure 2:
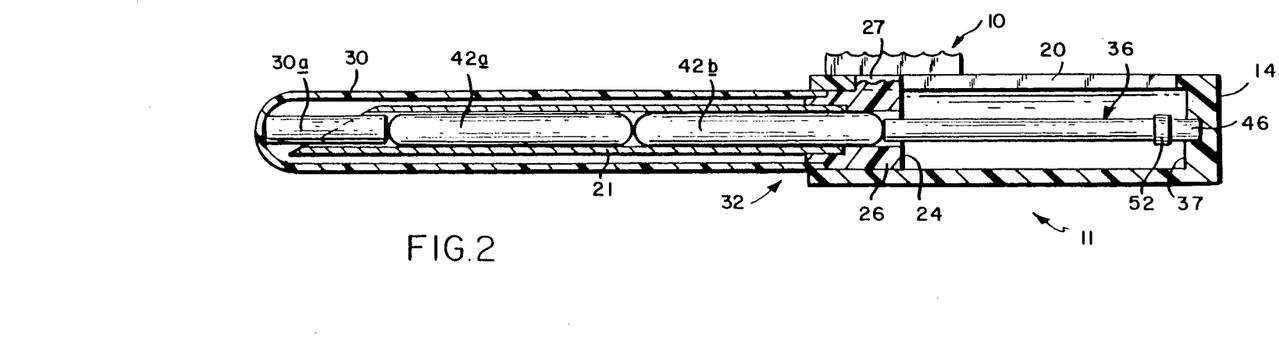
FIG. 2 is a side view of the injector, including a needle protector and the implant pellets.

FIG. 2 shows a side view of the barrel and needle assembly at section line 2—2 in FIG. 1. In the described embodiment, hub 26 is made of molded plastic, although other materials may be used. A circular rear opening 25 in hub 26 extends the bore of the cannula 21 through the hub. The rear opening is slightly smaller in diameter than the inside diameter of the cannula. A plurality of slots 29 extending from the opening 25 to the outside of hub 25 are formed to allow the rear opening to expand slightly, and these slots 29 cooperate with the obturator, as described in detail below, to enable multiple pellets to be implanted.

The hub 26 is attached to a knob 10 which is designed to be engaged by the thumb of a person operating the injector while the barrel is held cupped in the fingers. Knob 10 is attached to hub 26 via a connector piece 27. To assemble the needle assembly 12 and barrel 11, hub 26 is inserted in the open end 17 of the barrel. The connector piece 27 between the thumb knob 10 and the hub 26 slides through the front portion 15 of slot 20.

Figure 5:
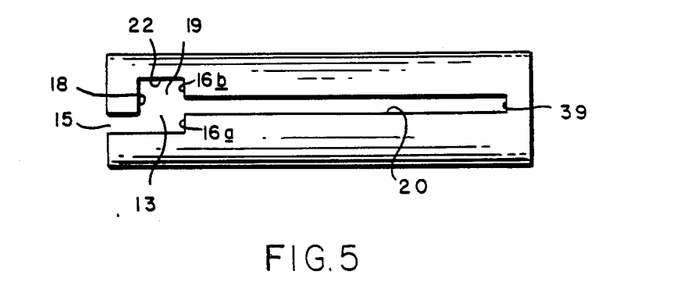
FIG. 5 shows the details of the slot in the injector barrel.

The configuration of slot 20 is shown in more detail in FIG. 5. In FIG. 5, the forward portion 15 of slot 20 opens into a notch area 13. Slot portion 15 forms the bottom wall of notch 13. Notch area 13 is bounded by rear walls 16a and 16b on either side of slot 20. A second portion 19 of notch 13 extends upwardly, as shown in FIG. 5, from the side of the notch. The second portion 19 is bounded by a front wall 18.

The distance from front wall 18 to rear wall 16b is such that the connection 27 between hub 26 and thumb knob 10 is a tight friction fit. The main portion of slot 20 extends rearwardly from the back walls 16 of the notch. During assembly, when the hub 26 is inserted into the open end 17 of barrel 11, the thumb knob connector 27 slides rearwardly into slot 15 until it abuts back wall 16a. The connector 27 and thumb knob 10 are then moved in an upward direction, with reference to FIG. 5, until the connector 27 abuts the top wall 22 of the notch. The dimensions of connector 27 and notch 13 are such that the frictional forces will hold the connector and hence hub 26 and cannula 21 in position between rear wall 16a and front wall 18 until the injector is to be used.

When the implanter is being used to implant pellets, the thumb knob 10 is used to move the connector 27 down from location 19 until it can slide backwards in slot 20. Slot 20 is wide enough to allow the thumb piece and needle assembly 12 to be moved forward and backward within the slot freely.

The width of slot 15 through which the connector piece 27 is inserted during assembly may be formed such that it is slightly narrower than the width of the connection piece 27. When this is done, slot 15 must be open slightly in order to insert the needle assembly 12. After the connection piece 27 has completely passed entry slot 15, the slot will close slightly to assume its original dimension. Since this dimension is slightly narrower than the width of connector 27, connection piece 27 and needle assembly 12 cannot be inadvertently slid out of the barrel through entry slot 15 during operation.

Returning to FIG. 2, barrel 11 and needle assembly 12 are shown after they have been assembled together and before the instrument is used. In FIG. 2, hub 26 is located inside barrel 11 with the connector 27 and thumb knob 10 extending through notch 13. An obturator 36, discussed in detail below, extends from the rear wall 14 of barrel 11 into the proximal end of hub 24. Obturator 36 fits into a recess 34 in the rear wall 14 of the barrel and is held in place by friction or other suitable means. The proximal portion of needle 21 is inserted into the front of hub 26 and fits in a recess therein. The opening 25 in the rear face of hub 26 has an inside diameter substantially the same as the inside diameter of the cannula 21. Thus, a continuous bore from the rear face 24 of hub 26 through the distal end of cannula 21 is formed.

Prior to being used, the implanter includes medicinal implant pellets 42a and 42b contained within the bore defined by cannula 21 and hub 26. Pellets 42a and 42b are substantially the same length and have an outside diameter which allows them to slide freely within the bore. The proximal end of the rearmost wall pellet 42b abuts the distal end of obturator 36. The distal end of the frontmost pellet 42a extends nearly to the distal end of cannula 21. Prior to being used, a cover 30 may be placed over the needle assembly 12. Cover 30 is maintained in place via a frictional fit over a front step 32 on hub 26. Cover 30 may include a plug 30a extending rearwardly from the distal end of the cover into the bore of cannula 21 to maintain pellets 42 in place. Cover 30 may serve to maintain the sterility of the device prior to being used and also to guard the sharp end of needle 23 to prevent accidents.

In the described embodiment, each of the implants 42 is 1.75 inches long. The length of barrel 11 from its front end 17 to the rear wall inside surface 37 is 2.60 inches.

The length of slot 20 from the rear walls 16 of the notch area 19 to the rear end 39 of slot 20 should be slightly longer than the length of the implants and is 1.85 inches in the described embodiment. The inside diameter of the barrel is about 0.350 inches and the outside diameter of hub 26 is 0.337 inches. The length of hub 26 along its axis is 0.625 inches and slots 29 extend forward for a distance of 0.125 inches from the rear of the hub. Additional dimensions are discussed below.

Figure 3:
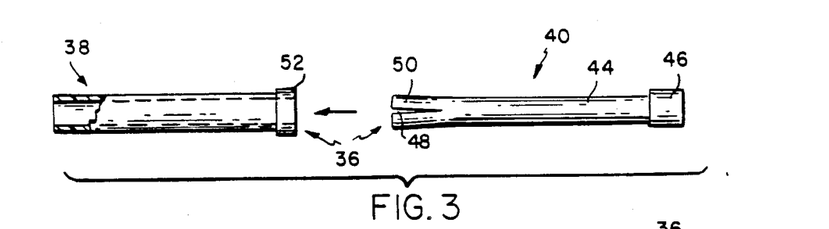
FIG. 3 shows the details of the two part obturator.

Referring to FIG. 3, th details of obturator 36 are shown. Obturator 36 is formed of two portions, including a hollow sleeve portion 38 and a solid core portion 40. Core portion includes a main shaft 44 and a base section 46. The base section 46 mounts in the recess 34 in the rear wall of the injector barrel, and the outside diameter of the base 46 is chosen appropriately, but must be no larger than the outside diameter of the main section of sleeve 38, as will become clear from the explanation below. The obturator sleeve 38 is hollow and cylindrical shaped with the inside diameter of the sleeve very slightly larger than the outside diameter of core portion 44 of the obturator core so that the core ma slide easily within the sleeve.

The end of the obturator core opposite the base 46 is split, as shown at 48. The split portion 48 extends a small distance back from the end of the core shaft 44. The split is such that the two sections in the end of the obturator core separated by the split 48 may be compressed so that they will fit within the bore of the obturator sleeve 38. When removed from the bore, however, the split opens up so that the outside diameter of end 50 of the obturator core is larger than the inside diameter of sleeve 38.

Figure 6A:
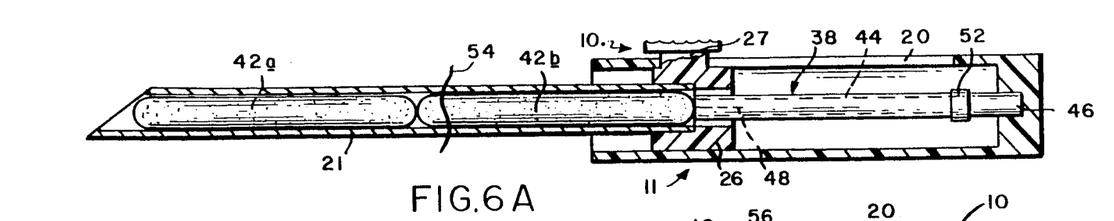
FIGS. 6A through 6D show the operation of the injector as it implants two pellets.

Sleeve 38 has a smooth inside bore of a substantially constant inside diameter. The outside diameter of sleeve portion 38 is likewise substantially constant, except for a small portion 52 at the rearmost end of the sleeve. The outside-diameter of portion 52 is slightly larger than the remainder of sleeve 38 for reasons which will be discussed below. The amount of enlargement of section 52 is greatly exaggerated in the drawings to illustrate the step more clearly. In the preferred embodiment, the outside diameter of the forward portion of sleeve 38 is 0.100 inches while the outside diameter of step 52 is 0.102 to 0.104 inches. Sleeve 38 is 1.85 inches long, as is the main shaft section 44 of the core 40. Base section 46 is slightly longer than the depth of recess 34, as shown in FIGS. 2 and 6.

Figure 4A:
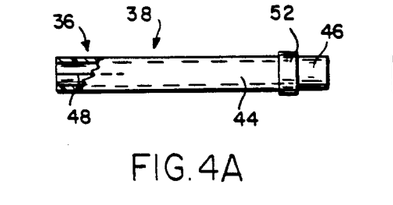
FIGS. 4A and 4B show the obturator in its assembled form.
Figure 4B:
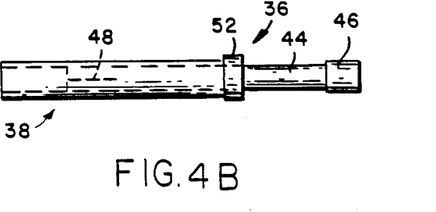

FIGS. 4A and 4B show the obturator when core 40 is inserted within sleeve 38. FIG. 4A represents the obturator with the core 40 fully inside sleeve 38, corresponding to the arrangement shown fully in FIG. 2. FIG. 4B shows the obturator core partially extending from sleeve 38. In both FIGS. 4A and 4B, it can be seen that the core split 48 has been compressed to fit inside the bore of the obturator sleeve.

Figure 7:
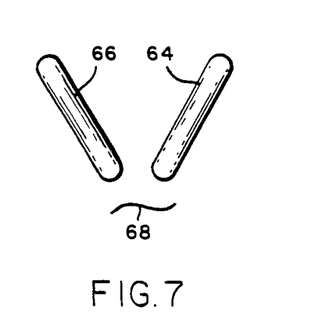
FIG. 7 illustrates the desired fan shaped placement of the two implant pellets.

FIG. 7 shows the preferred orientation for two implants. In FIG. 7, two implants 64 and 66 are located in a fan shaped pattern side by side. It is important that the implants be spaced far enough apart that the implants do not interfere with the release of the drug by the other implants. It is also desirable to perform the implantation of both pellets through a single incision or opening 68 through the patient's skin.

FIGS. 6A through 6D show succeeding stages in the operation of the injector and how it would be used to subcutaneously place implants beneath the skin of the patient in the fan pattern shown in FIG. 7. As shown in FIG. 2, FIG. 6A has two implants 42a and 42b located within the cannula 21. The hub 26 is located at the forward end of slot 20. The obturator core 40 is fully inserted within the bore of obturator sleeve 38, and the obturator assembly 36 extends from the rear wall 14 of barrel 11 into the back of hub 26. Obturator 36 is in contact with rearmost pellet 42b which in turn is in contact with pellet 42a at the distal end of cannula 21. With the injector disposed as shown in FIG. 6A, the beveled end 23 of the cannula is inserted beneath the skin of a patient. With the distal tip of cannula 21 beneath the skin of a patient, the injector is manipulated to insert cannula 21 further beneath the skin until the forward implant 42a is in the desired location. At this point, the incision in the patient's skin through which the cannula is inserted should be located a small distance behind the distal end of the rear insert 42b, as shown by incision line 54 in FIG. 6A. The engagement of the connecting piece 27 within notch 19 of the slot 42b aids the operator in keeping the rear hub 26 stationary with respect to barrel 11 during the process of inserting the cannula subcutaneously.

Figure 6B:
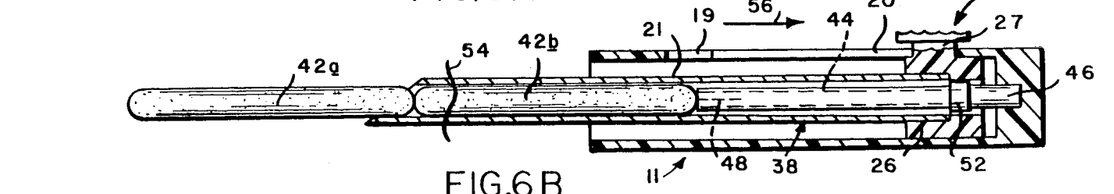

After the operator is satisfied that the formost implant 42a is properly located, hub 26 is disengaged from notch 19 and moved rearwardly in slot 20. This is shown in FIG. 6B in which arrow 56 indicates the rearward motion of hub 26. This rearward motion maybe quickly and easily accomplished by means of a thumb on the thumb-knob 10 while the barrel is held stationary by the operator's fingers. As hub 26 is moved rearwardly, cannula 21 also moves rearwardly and retracts from around the first implant 42a, leaving it in the desired location.

Hub 26 is moved all the way rearwards in slot 20 until connection piece 27 abuts against the rear wall 39 of slot 20, to give the configuration shown in FIG. 6B. In FIG. 6B, the formost implant 42a has been subcutaneously placed in the desired location and is substantially disengaged from the bore of cannula 21, as shown in FIG. 6B. The distal end of cannula 21 still extends for a small distance under the patient's skin through the incision 54. At this point, the injector operator would withdraw the entire injector a small amount to ensure that the end of cannula 21 is fully disengaged from implant 42A. The end of the cannula remains under the skin and within incision 54.

Figure 6C:
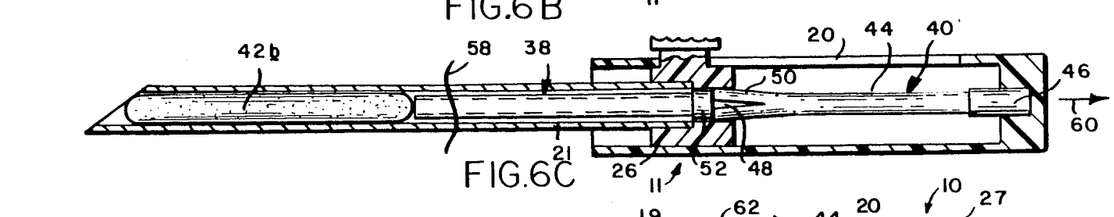

Next, the operator would move the barrel 11 backward with respect to hub 26, as shown by arrow 60 in FIG. 6C. With the present invention, this may be easily done by holding the barrel 11 in the fingers of one hand and moving it rearwardly while maintaining the hub and cannula in a fixed position with respect to the patient and with respect to the incision 54. The barrel is moved rearwardly until the connecting section 27 again contacts the front wall of notch 19 so that the configuration of the injector is as shown in FIG. 6C with the end of the injector still slightly within the incision 54 and carrying the second implant 42b.

When hub 26 is moved rearwardly to provide the configuration shown in FIG. 6B, the rear face 24 of the hub passes over the enlarged portion 52 of the obturator sleeve 38. The inside diameter of the rear opening 25 in hub 26 is normally slightly smaller than the outside diameter of enlarged portion 52. In the described embodiment, the diameter of opening 25 is 0.098 inches. The slots 29 in hub 26 allow it to open slightly and pass over the enlarged section 52 of the obturator sleeve. As hub 26 is moved forward to go from the configuration of FIG. 6B to that of FIG. 6C, it carries the outer sleeve 38 of the obturator forward due to the frictional forces between the enlarged section 52 of the obturator sleeve and the inside the hub rear opening 25. The dimensions of the implanter are such that when the hub 26 is moved to its forwardmost position, the rear of the obturator sleeve 38 is moved forward past the end of the obturator core 40. At this point, the split 48 in the end of the obturator core is no longer constrained by the inner walls of the obturator sleeve and expands, as shown in FIG. 6C.

With the tip of the cannula extending slightly through incision 54 as shown in FIG. 6C, the injector is then pivoted while keeping the distal end of the cannula within incision 54 so that the second implant 42b may be inserted next to the first implant in the previously described fan shaped pattern. After being pivoted, the injector is moved forward through the incision to locate the second implant 42b beneath the skin of the patient. As the cannula is pushed beneath the skin to locate the second implant 42b, the incision moves from location 54 to location 58 on the cannula so that the second implant 42b is located entirely beneath the skin and is surrounded by the cannula 21.

Figure 6D:
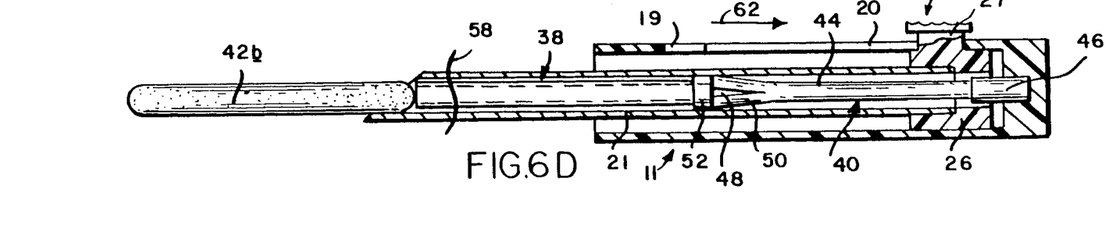

To finish the implantation process for the second implant, the hub is once more moved rearwardly with respect to the barrel 11, as shown by arrow 62 in FIG. 6D. The frictional force between the expanded portion 52 of the obturator sleeve 38 and the inside of hub 26 is overcome to allow hub 26 and attached cannula 21 to slide backward past the expanded portion 52 which is held in the forward position shown in FIGS. 6C and 6D by the split end 50 of the obturator core 40.

As the hub 26 is moved to its rearwardmost position within barrel 11, the cannula 21 moves rearwardly leaving the implant 42b underneath the skin in the desired position. After the hub 26 has been moved all the way rearwardly, the disposition of the implanter and the implant 42b are as shown in FIG. 6D. At this point, the instrument is withdrawn from the incision 58 and the implantation procedure is completed.

To summarize the operation of the injector and telescoping obturator, as the hub is moved from the rearward position shown in FIG. 6B to the forward position shown in Fig. 6C, the friction between the hub rear opening 25 and the enlarged portion 52 of the obturator's sleeve causes the sleeve to be carried forward by the hub until it clears the obturator core 40. Once the split end 50 of the obturator core 40 is no longer constrained by the obturator's sleeve 38, it opens and prevents the obturator 38 from moving rearwardly. As the hub 26 is moved rearwardly from the position shown in FIG. 6C to the position shown in FIG. 6D, the forward pressure on the obturator's sleeve 38 by the obturator core 40 is sufficient to overcome the frictional forces between the hub 26 and the enlarged portion 52 of the obturator's sleeve. Typically, the inside diameter of the cannula 21 is slightly larger than the outside diameter of the enlarged portion 52, although this is not shown in the drawings. In the preferred embodiment, the cannula has an inside diameter of 0.106 inches while hub 26 has an inside diameter of 0.098 inches. Thus, as the hub 26 is moved rearwardly, the enlarged portion 52 passes from within the hub rear openinq 25 to the proximal end of cannula 21. The frictional forces between the enlarged portion 52 and needle assembly 12 are eliminated, allowing the hub to be moved rearwardly by the operator with ease.

The present invention may be manufactured inexpensively enough so that the injector and implants can be supplied as a pre-sterilized sealed package with the injector to be discarded after being used once. This is especially important if the invention is used in remote or underdeveloped areas where sterile conditions may be hard to maintain.

It should also be apparent that the obturator can comprise more than two sections where it is desired to. implant more than two pellets. For example, a three-part telescoping obturator would be used to locate and expel from the cannula three implant pellets.

Figure 8:
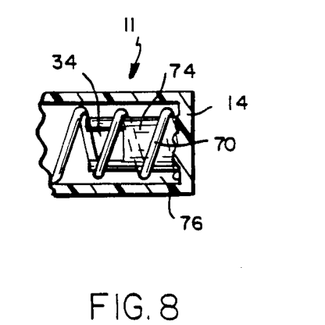
FIG. 8 shows an alternate embodiment of the present invention.

Referring to FIG. 8, there is shown an alternate embodiment of the present invention. FIG. 8 depicts the rearmost portion of barrel 11. In FIG. 8, a spring 70 has been added to the apparatus. The spring 70 extends from the rear wall 14 of the obturator barrel to the rear face 24 of the hub 26 (not shown in FIG. 8). The spring serves to provide a force to maintain the hub in a forward position within slot 19 prior to being used, and further allows an operator to move the barrel 11 rearward with respect to the needle assembly 12, as shown in FIG. 6B, by relaxing slightly the grip of the operator's fingers upon the barrel so that the spring 70 will provide a force to move the barrel in a backward direction. To provide room for spring 70 when it is compressed between the hub and the back wall 14 of the barrel 11, the barrel may be extended rearwardly, as shown in FIG. 8. An extension 74 has been added between the obturator base 46 and the rear wall 14 of the barrel. The base 46 of the obturator fits within recess 34. A cylindrical space 76 between the extension 74 and the outside walls of the extended barrel 11 provides space for spring 70 as it is compressed when the hub and cannula are moved rearwardly.

There has been described a new and unique apparatus for administering multiple subcutaneous implants to a patient which has advantages over devices for performing similar functions which have previously been known. It should be appreciated that in applying the teachings of the invention to different situations, those of ordinary skill in the art will make modifications to the embodiments described above. Accordingly, the invention should not be taken as being limited by the foregoing discussion of the preferred embodiments, but rather should be interpreted only in accordance with the following claims.

What is claimed is:

1. A device for inserting and positioning a plurality of elongate implants beneath the skin, comprising:
   a long, hollow cannula adapted for insertion beneath the skin;
   a hub to which the cannula is attached so as to define a continuous bore sufficiently long to contain said plurality of implants in an end-to-end relationship;
   a hollow body within which said hub is slidably mounted so as to move between a proximal and a distal position along an axis parallel to the continuous bore;
   an obturator having distal and proximal ends and including first and second sections which are connected so as to allow the first section to move with respect to the second section;
   means for mounting the obturator first section to the hollow body so that the continuous bore slides over the obturator as the hub is moved between the distal and proximal positions;

the hub and obturator further including means for the hub to engage the obturator second section when the hub is first moved from the distal position to the proximal position and for moving the obturator second section in a distal direction to an extended position as the hub is subsequently moved from the proximal position to the distal position; and means, operative after the hub has been moved from the proximal position to the distal position, for maintaining the obturator second section in said extended position as the hub is moved from the distal position towards the proximal position.

2. The apparatus of claim 1 wherein one of the obturator sections slides within the other section so that the obturator elongates by telescoping as the first section moves with respect to the second section.

3. The apparatus of claim 1 wherein the obturator first section is cylindrical and wherein the obturator second section includes a cylindrical bore adapted to slide over the obturator first section.

4. The apparatus of claim 3 wherein the obturator first section includes:

a cylindrical rod having a slit in the distal end thereof which forms at least two opposing legs;

means for applying a force to the opposing legs which tends to separate the legs;

and wherein the length of the obturator first and second sections is such that the legs are constrained within the bore of the obturator second section until the insertion means is moved from the proximal position to the distal position and are free, when the insertion means reaches the distal position, to extend outwardly beyond the cylindrical bore of the obturator second section thereby preventing the second section from moving in a proximal direction once the hub has been moved from the proximal to the distal position.

5. The apparatus of claim 1 wherein the body includes a cylindrical barrel having a closed proximal end to which the obturator first section is mounted and an open distal end.

6. The apparatus of claim 5 wherein the body includes a slot in the body having distal and proximal end walls and extending in a direction parallel to the continuous bore;

and wherein the hub includes a manually-actuable knob extending through said slot and being constructed so that the knob abuts the distal and proximal ends of the slot respectively when the hub is in the distal and proximal positions.

7. The apparatus of claim 6 wherein the hub includes a plastic cylindrical portion having a metal cannula attached thereto, said manually-actuable knob being formed as an extension of the hub.

8. The apparatus of claim 6 wherein the body includes an opening extending from the open distal end of the housing to the distal wall of the slot to allow the hub knob to be inserted within said slot.

9. The apparatus of claim 6 wherein the body includes a notch at the distal end of said slot and means associated with said notch for frictionally retaining the knob within the notch prior to use of said apparatus.

10. The apparatus of claim 3 wherein the obturator second section includes a cylinder with an enlarged outer diameter portion at the proximal end thereof;

and wherein the hub has a metal cannula attached thereto, the hub including a cylindrical opening parallel and contiguous to the cannula bore and of a diameter substantially the same as said enlarged outer diameter portion of the obturator second section, said opening having means adapted to slide over said enlarged outer diameter portion and for providing a frictional interface between the hub opening walls and the enlarged outer diameter portion;

whereby the obturator second section is moved distally with respect to the obturator first portion as the hub is moved from the proximal position to the distal position.

11. A device for inserting and positioning a plurality of elongate implants beneath the skin, comprising:

insertion means for defining a bore, the bore being sufficiently long to contain the plurality of implants in an end-to-end relationship and including a hollow cannula adapted for insertion beneath the skin, the cannula having a bore which forms at least a part of said insertion means bore;

an obturator having distal and proximal ends and including first and second sections which are connected so as to allow the first section to move with respect to the second section, the direction of movement being along an obturator axis;

body means for positioning the obturator with respect to the insertion means bore so that the distal end of the obturator lies within the insertion means bore and so that the obturator axis is substantially parallel with the insertion means bore;

means for moving the insertion means with respect to the obturator first section between a distal position and a proximal position;

the insertion means further including means for engaging the obturator second section when the insertion means is first moved from the distal position to the proximal position and for moving the obturator second section in a distal direction to an extended position as the insertion means is subsequently moved from the proximal position to the distal position; and means, operative after the insertion means have been moved from the proximal position to the distal position, for maintaining the obturator second section in said extended position as the insertion means is moved from the distal position towards the proximal position; and wherein the body means includes a hollow housing having a closed proximal end and an open distal end within which the insertion means is slidably mounted.

12. The apparatus of claim 11 wherein the means for moving includes:

a slot in said housing having distal and proximal end walls and extending in a direction parallel to the insertion means bore;

a manually-actuable knob extending through said slot and being constructed so that the knob abuts the distal and proximal end walls of the slot respectively when the insertion means is in the distal and proximal positions.

13. The apparatus of claim 12 wherein the insertion means further includes a plastic hub having a metal cannula attached thereto, the hub including a cylindrical opening parallel and contiguous to the cannula bore, said manually-actuable knob being formed as an extension of the hub.

14. The apparatus of claim 12 wherein the housing includes an opening extending from the open distal end of the housing to the distal wall of the slot to allow the insertion means knob to be inserted within said slot.

15. The apparatus of claim 12 wherein the housing includes a notch at the distal end of said slot and means associated with said notch for frictionally retaining the knob within the notch prior to use of said apparatus.

16. The apparatus of claim 14 wherein the obturator second section includes a cylinder with an enlarged outer diameter portion at the proximal end thereof;

and wherein the insertion means includes a hub having a metal cannula attached thereto, the hub including a cylindrical opening parallel and continuous to the cannula bore and of a diameter substantially the same as said enlarged outer diameter portion of the obturator second section, said openinq having means adapted to slide over said enlarged outer diameter portion and for providing a frictional interface between the hub opening walls and the enlarged outer diameter portion when the insertion means is moved to the proximal position; whereby the obturator second section is moved distally with respect to the obturator first section as the insertion means is moved from the proximal position to the distal position.

* * * * *

UNITED STATES PATENT AND TRADEMARK OFFICE
CERTIFICATE OF CORRECTION

PATENT NO. : 4,846,793

DATED : July 11, 1989

INVENTOR(S) : Robert J. Leonard, S. Mitchell Harman

It is certified that error appears in the above-identified patent and that said Letters Patent is hereby corrected as shown below:

Column 1, lines 52-53, change "psycholoquical" to --psychological--.

Column 2, line 59, change "th" to --the--.

Column 3, lines 49-50, change "openingq" to --opening--.

Column 5, line 10, change "th" to --the--.

Column 5, line 23, change "ma" to --may--.

Column 6, line 20, change "42b" to --20--.

Column 6, line 27, change "maybe" to --may be--.

Column 7, line 64, change "openinq" to --opening--.

In claim 16, column 11, line 7, change "14" to --11--.

Signed and Sealed this

Twenty-sixth Day of June, 1990

Attest:

HARRY F. MANBECK, JR.

*Attesting Officer*     *Commissioner of Patents and Trademarks*